(12) United States Patent
Xu et al.

(10) Patent No.: US 7,575,373 B2
(45) Date of Patent: Aug. 18, 2009

(54) CASSETTE TRAY AND X-RAY IMAGING APPARATUS

(75) Inventors: Jiake Xu, Beijing (CN); Yong Xu, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 12/339,747

(22) Filed: Dec. 19, 2008

(65) Prior Publication Data

US 2009/0168970 A1 Jul. 2, 2009

(51) Int. Cl.
 *G03B 42/02* (2006.01)
 *A61B 6/14* (2006.01)
(52) U.S. Cl. ...................... 378/172; 378/169
(58) Field of Classification Search .......... 378/167–175
 See application file for complete search history.

(56) References Cited

U.S. PATENT DOCUMENTS

| | | | |
|---|---|---|---|
| 3,920,997 A | 11/1975 | Munch | |
| 4,232,227 A * | 11/1980 | Finkenzeller et al. | 378/177 |
| 4,760,641 A | 8/1988 | Gandolfo | |
| 4,893,322 A * | 1/1990 | Hellmick et al. | 378/173 |
| 4,961,213 A * | 10/1990 | Linhart | 378/181 |
| 5,138,160 A | 8/1992 | Shimizu et al. | |
| 5,330,309 A * | 7/1994 | Brahm et al. | 414/411 |
| 5,465,285 A | 11/1995 | Gall et al. | |
| 6,126,314 A | 10/2000 | Morasse | |
| 6,176,364 B1 | 1/2001 | Hoitz et al. | |
| 6,278,126 B2 | 8/2001 | Hoitz | |
| 6,811,311 B2 | 11/2004 | Hayes et al. | |
| 7,097,355 B2 | 8/2006 | Araki et al. | |
| 7,137,735 B2 | 11/2006 | Araki et al. | |
| 7,368,747 B2 | 5/2008 | Kralles et al. | |
| 2001/0006223 A1 | 7/2001 | Hoitz | |

FOREIGN PATENT DOCUMENTS

JP     2005-195653     7/2005

* cited by examiner

*Primary Examiner*—Irakli Kiknadze
(74) *Attorney, Agent, or Firm*—Armstrong Teasdale LLP (57) ABSTRACT

A cassette tray includes a front clamp, a rear clamp, and opposing side clamps. A front clamp supporting unit supports the front clamp such that the front clamp may be moved in a direction vertical to a surface of the X-ray film cassette. A rear clamp supporting unit supports the rear clamp such that the rear clamp may be moved in a direction parallel to the surface of the X-ray film cassette. A side clamp supporting unit supports the side clamps such that the side clamps may be moved in a direction in which the side clamps are apart from each other and in a direction in which the side clamps are close to each other, wherein the side clamps are driven by a driving unit according to the advance and retreat of the rear clamp.

20 Claims, 8 Drawing Sheets

CASSETTE TRAY AND X-RAY IMAGING APPARATUS

CROSS REFERENCE TO RELATED APPLICATIONS

This application claims the benefit of Chinese Patent Application No. 200710185760.4 filed Dec. 28, 2007, which is hereby incorporated by reference in its entirety.

BACKGROUND OF THE INVENTION

The subject matter disclosed herein relates to a cassette tray and an X-ray imaging apparatus, and more particularly, to a cassette tray that regulates and holds an X-ray film cassette by four sides, and an X-ray imaging apparatus having the cassette tray.

An X-ray imaging apparatus irradiates an X-ray to a patient from an X-ray irradiator, and detects the transmitted X-ray by an X-ray detector so as to form a fluoroscopic image. A subject to be imaged faces the X-ray detector between the X-ray irradiator and the X-ray detector.

Some of the X-ray imaging apparatuses take an X-ray fluoroscopic image by using an X-ray film cassette. The imaging is performed with the state in which the X-ray film cassette is loaded to a cassette tray. The cassette tray is configured to regulate and hold the X-ray film cassette by four sides (see, for example, Japanese Unexamined Patent Publication No. 2005-195653).

BRIEF DESCRIPTION OF THE INVENTION

The cassette tray of this type has a mechanism driven by a motor, and this mechanism is controlled by electronics. Therefore, the configuration of the cassette tray is made complicated.

Accordingly, the embodiments described herein realize a cassette tray having a simple structure, and an X-ray imaging apparatus having the cassette tray.

According to one aspect, the invention for solving the subject is a cassette tray that regulates and holds an X-ray film cassette by four sides, and that includes a front clamp, a rear clamp, and clamps at both sides, which clamp the front side, rear side and both sides of the X-ray film cassette when it is held; front clamp supporting unit that supports the front clamp so as to be capable of being withdrawn and returned in the direction vertical to the surface of the X-ray film cassette; rear clamp supporting unit that supports the rear clamp so as to be advanced and retreated in the direction parallel to the surface of the X-ray film cassette; both-side clamp supporting unit that supports the clamps at both sides so as to be movable in the direction in which the clamps at both sides are apart from each other and in the direction in which the clamps at both sides are close to each other; and driving unit that drives a spring in the direction in which the clamps at both sides are apart from each other and in the direction in which the clamps at both sides are close to each other according to the advance and retreat of the rear clamp.

According to the second aspect, the invention for solving the subject is the film cassette, described in the first aspect, wherein the front clamp and the rear clamp are opposite and parallel to each other, and the clamps at both sides are opposite and parallel to each other.

According to the third aspect, the invention for solving the subject is the film cassette, described in the second aspect, wherein the clamps at both sides have a guide for loading the X-ray film cassette.

According to the fourth aspect, the invention for solving the subject is the film cassette, described in the first aspect, wherein the front clamp supporting unit includes a flip board for supporting the front clamp, and a spring that applies returning force to the flip board.

According to the fifth aspect, the invention for solving the subject is the film cassette, described in the first aspect, wherein the rear clamp supporting unit has a linear rail for the advance and retreat of the rear clamp.

According to the sixth aspect, the invention for solving the subject is the film cassette, described in first aspect, wherein the both-side clamp supporting unit has a linear rail for the movement of the clamps at both sides.

According to the seventh aspect, the invention for solving the subject is the film cassette, described in the first aspect, wherein the both-side clamp supporting unit has two pulleys arranged at a space greater than the width of the X-ray film cassette, and a wire that is endlessly put around the two pulleys, and to which one of the clamps at both sides and the other thereof are coupled in such a manner that the moving directions caused the rotation of the pulleys are reverse to each other.

According to the eighth aspect, the invention for solving the subject is the film cassette, described in the first aspect, wherein the driving unit has a lever that can be rotated in a plane parallel to the surface of the X-ray film cassette, wherein the lever has at its one end a longitudinal slit that is engaged with a pin, which moves with the rear clamp, and has at its other end a spring that is coupled to one of the clamps at both sides.

According to the ninth aspect, the invention for solving the subject is the film cassette, described in the eighth aspect, wherein the spring is a damper spring.

According to the tenth aspect, the invention for solving the subject is the film cassette, described in the first aspect, including moving unit that integrally moves the front clamp supporting unit, the rear clamp supporting unit, the both-side clamp supporting unit, and the driving unit.

According to the eleventh aspect, the invention for solving the subject is an X-ray imaging apparatus that images an X-ray fluoroscopic image by an X-ray film cassette loaded to a cassette tray, the cassette tray including a front clamp, a rear clamp, and clamps at both sides, which clamp the front side, rear side and both sides of the X-ray film cassette when it is held; front clamp supporting unit that supports the front clamp so as to be capable of being withdrawn and returned in the direction vertical to the surface of the X-ray film cassette; rear clamp supporting unit that supports the rear clamp so as to be advanced and retreated in the direction parallel to the surface of the X-ray film cassette; both-side clamp supporting unit that supports the clamps at both sides so as to be movable in the direction in which the clamps at both sides are apart from each other and in the direction in which the clamps at both sides are close to each other; and driving unit that drives a spring in the direction in which the clamps at both sides are apart from each other and in the direction in which the clamps at both sides are close to each other according to the advance and retreat of the rear clamp.

According to the twelfth aspect, the invention for solving the subject is an X-ray imaging apparatus, described in the eleventh aspect, wherein the front clamp and the rear clamp are opposite and parallel to each other, and the clamps at both sides are opposite and parallel to each other.

According to the thirteenth aspect, the invention for solving the subject is an X-ray imaging apparatus, described in the twelfth aspect, wherein the clamps at both sides have a guide for loading the X-ray film cassette.

According to the fourteenth aspect, the invention for solving the subject is an X-ray imaging apparatus, described in the eleventh aspect, wherein the front clamp supporting unit includes a flip board for supporting the front clamp, and a spring that applies returning force to the flip board.

According to the fifteenth aspect, the invention for solving the subject is an X-ray imaging apparatus, described in the eleventh aspect, wherein the rear clamp supporting unit has a linear rail for the advance and retreat of the rear clamp.

According to the sixteenth aspect, the invention for solving the subject is an X-ray imaging apparatus, described in the eleventh aspect, wherein the both-side clamp supporting unit has a linear rail for the movement of the clamps at both sides.

According to the seventeenth aspect, the invention for solving the subject is an X-ray imaging apparatus, described in the eleventh aspect, wherein the both-side clamp supporting unit has two pulleys arranged at a space greater than the width of the X-ray film cassette, and a wire that is endlessly put around the two pulleys, and to which one of the clamps at both sides and the other thereof are coupled in such a manner that the moving directions caused by the rotation of the pulleys are reverse to each other.

According to the eighteenth aspect, the invention for solving the subject is an X-ray imaging apparatus, described in the eleventh aspect, wherein the driving unit has a lever that can be rotated in a plane parallel to the surface of the X-ray film cassette, wherein the lever has at its one end a longitudinal slit that is engaged with a pin, which moves with the rear clamp, and has at its other end a spring that is coupled to one of the clamps at both sides.

According to the nineteenth aspect, the invention for solving the subject is an X-ray imaging apparatus, described in the eleventh aspect, wherein the spring is a damper spring.

According to the twentieth aspect, the invention for solving the subject is an X-ray imaging apparatus, described in the eleventh aspect, including moving unit that integrally moves the front clamp supporting unit, the rear clamp supporting unit, the both-side clamp supporting unit, and the driving unit.

According to the present invention, a cassette tray includes a front clamp, a rear clamp, and clamps at both sides, which clamp the front side, rear side and both sides of the X-ray film cassette when it is held; front clamp supporting unit that supports the front clamp so as to be capable of being withdrawn and returned in the direction vertical to the surface of the X-ray film cassette; rear clamp supporting unit that supports the rear clamp so as to be advanced and retreated in the direction parallel to the surface of the X-ray film cassette; both-side clamp supporting unit that supports the clamps at both sides so as to be movable in the direction in which the clamps at both sides are apart from each other and in the direction in which the clamps at both sides are close to each other; and driving unit that drives a spring in the direction in which the clamps at both sides are apart from each other and in the direction in which the clamps at both sides are close to each other according to the advance and retreat of the rear clamp. Therefore, a cassette tray having a simplified structure and an X-ray imaging apparatus having the cassette tray can be realized.

Since the front clamp and the rear clamp are opposite and parallel to each other, and the clamps at both sides are opposite and parallel to each other, the X-ray film cassette can suitably be clamped.

Since the clamps at both sides have a guide for loading the X-ray film cassette, the X-ray film cassette can easily be loaded.

Since the front clamp supporting unit includes a flip board for supporting the front clamp, and a spring that applies returning force to the flip board, the front clamp can easily be withdrawn and returned.

Since the rear clamp supporting unit has a linear rail for the advance and retreat of the rear clamp, the rear clamp can smoothly be advanced and retreated.

Since the both-side clamp supporting unit has a linear rail for the movement of the clamps at both sides, the clamps at both sides can smoothly be moved.

The both-side clamp supporting unit has two pulleys arranged at a space greater than the width of the X-ray film cassette, and a wire that is endlessly put around the two pulleys, and to which one of the clamps at both sides and the other thereof are coupled in such a manner that the moving directions caused the rotation of the pulleys are reverse to each other. Therefore, the clamps at both sides can easily be moved in the direction in which they are apart from each other and in the direction in which they are close to each other.

The driving unit has a lever that can be rotated in a plane parallel to the surface of the X-ray film cassette, wherein the lever has at its one end a longitudinal slit that is engaged with a pin, which moves with the rear clamp, and has at its other end a spring that is coupled to one of the clamps at both sides. Therefore, the clamps at both sides can easily be moved in the direction in which they are apart from each other and in the direction in which they are close to each other, according to the advance and retreat of the rear clamp.

Since the spring is a damper spring, the X-ray film cassette is prevented from popping out when it is unloaded.

Since the present invention includes moving unit that integrally moves the front clamp supporting unit, the rear clamp supporting unit, the both-side clamp supporting unit, and the driving unit, the film cassette can appropriately be moved to the imaging position and retreated from the imaging position.

DETAILED DESCRIPTION OF THE INVENTION

Figure 1:
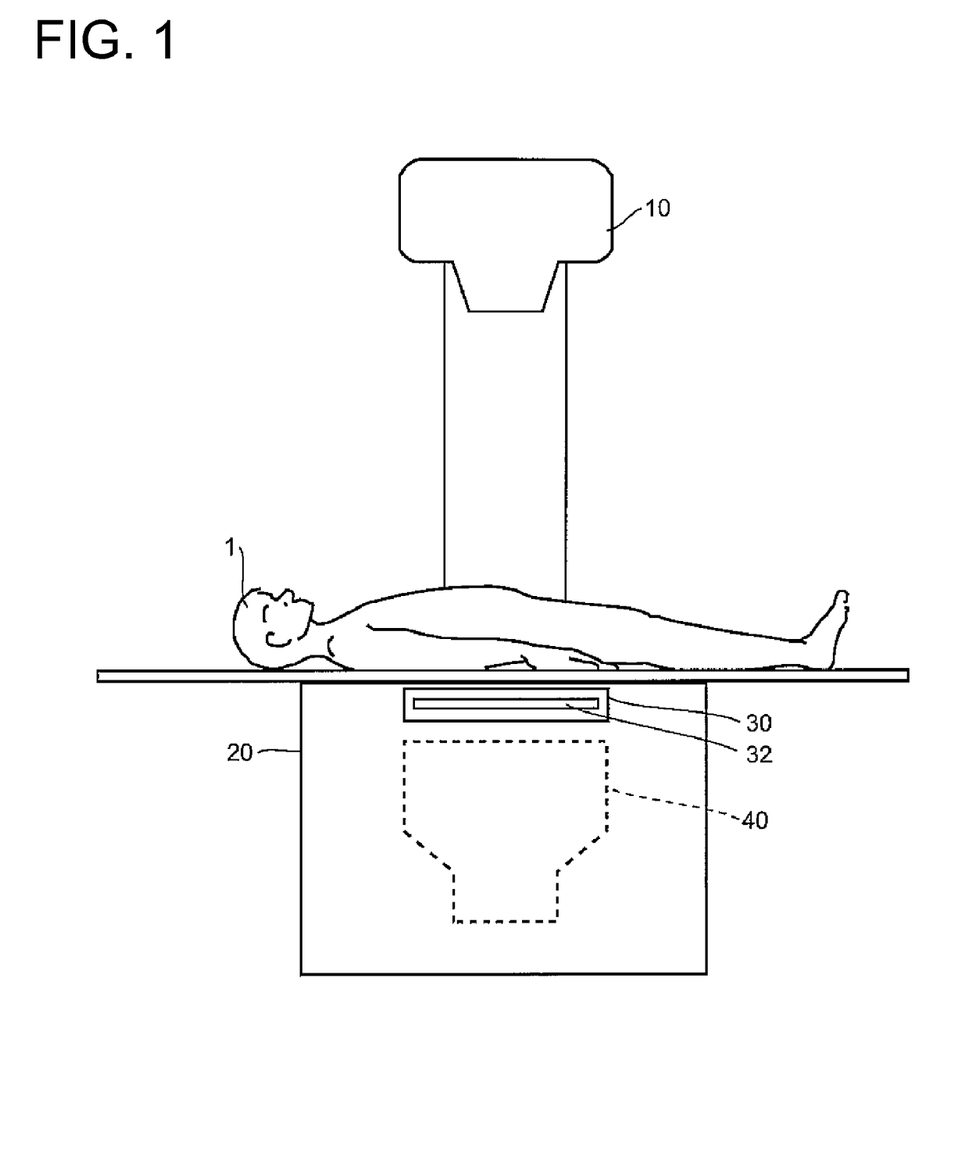
FIG. 1 is a view showing a configuration of an exemplary X-ray imaging apparatus.

Various embodiments of the present invention will be explained in detail with reference to the drawings. The present invention is not limited to the embodiments described herein. FIG. 1 schematically shows the configuration of an exemplary X-ray imaging apparatus.

As shown in FIG. 1, the present apparatus irradiates an X-ray to a subject 1 on an imaging table 20 from an X-ray irradiator 10, and takes a fluoroscopic image by unit of an X-ray film cassette 32 loaded to a cassette tray 30 in the imaging table 20.

The present apparatus has an X-ray detector 40 in the imaging table 20, and can carry out a digital radiography or a digital fluoroscopy by using the X-ray detector 40.

FIGS. 2 to 5 show the configuration of an exemplary cassette tray 30 that may be used with the X0-ray imaging apparatus shown in FIG. 1.

Figure 2:
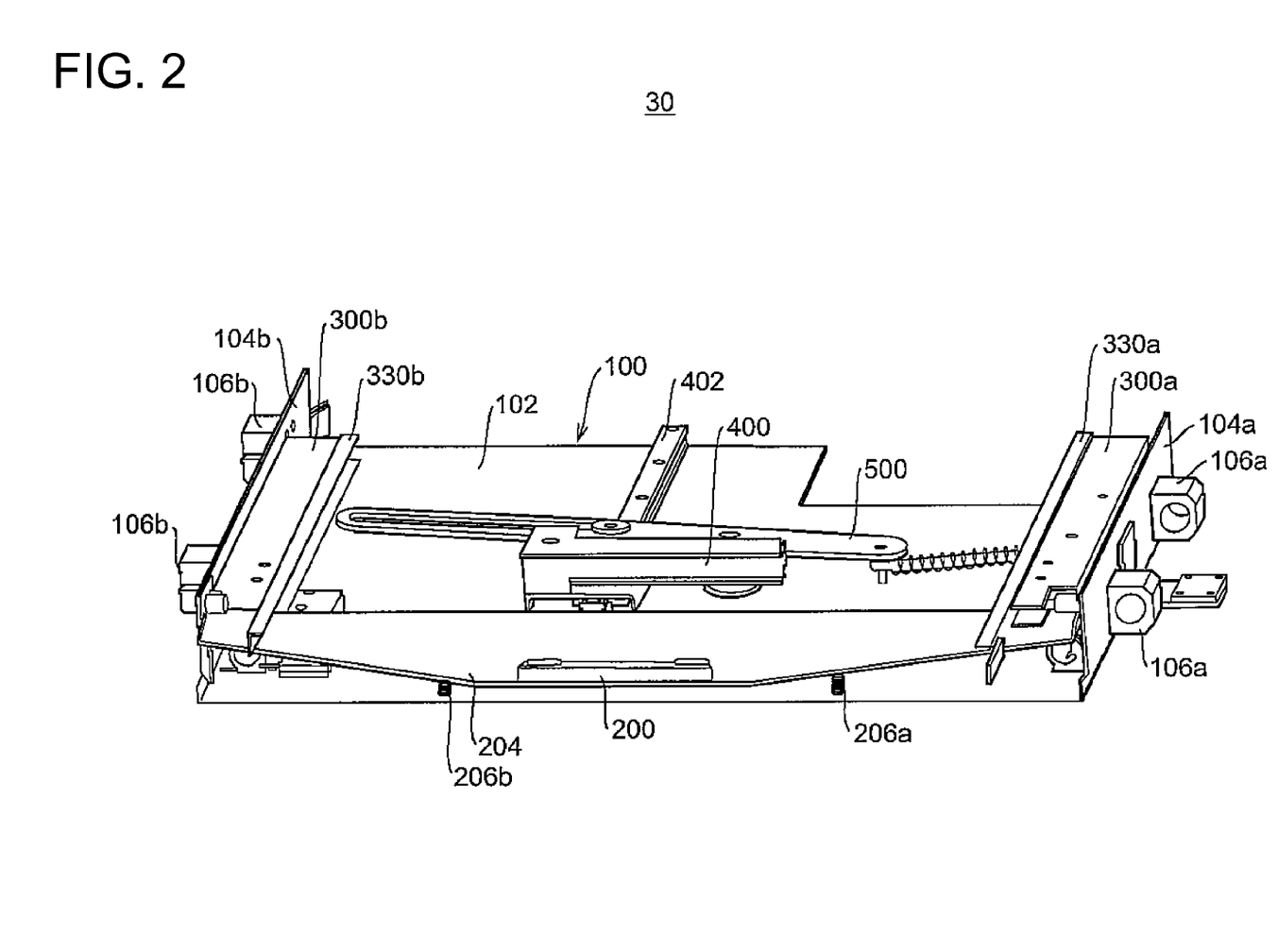
FIG. 2 is a perspective view showing a configuration of an exemplary cassette tray that may be used with the X-ray imaging apparatus shown in FIG. 1.
Figure 3:
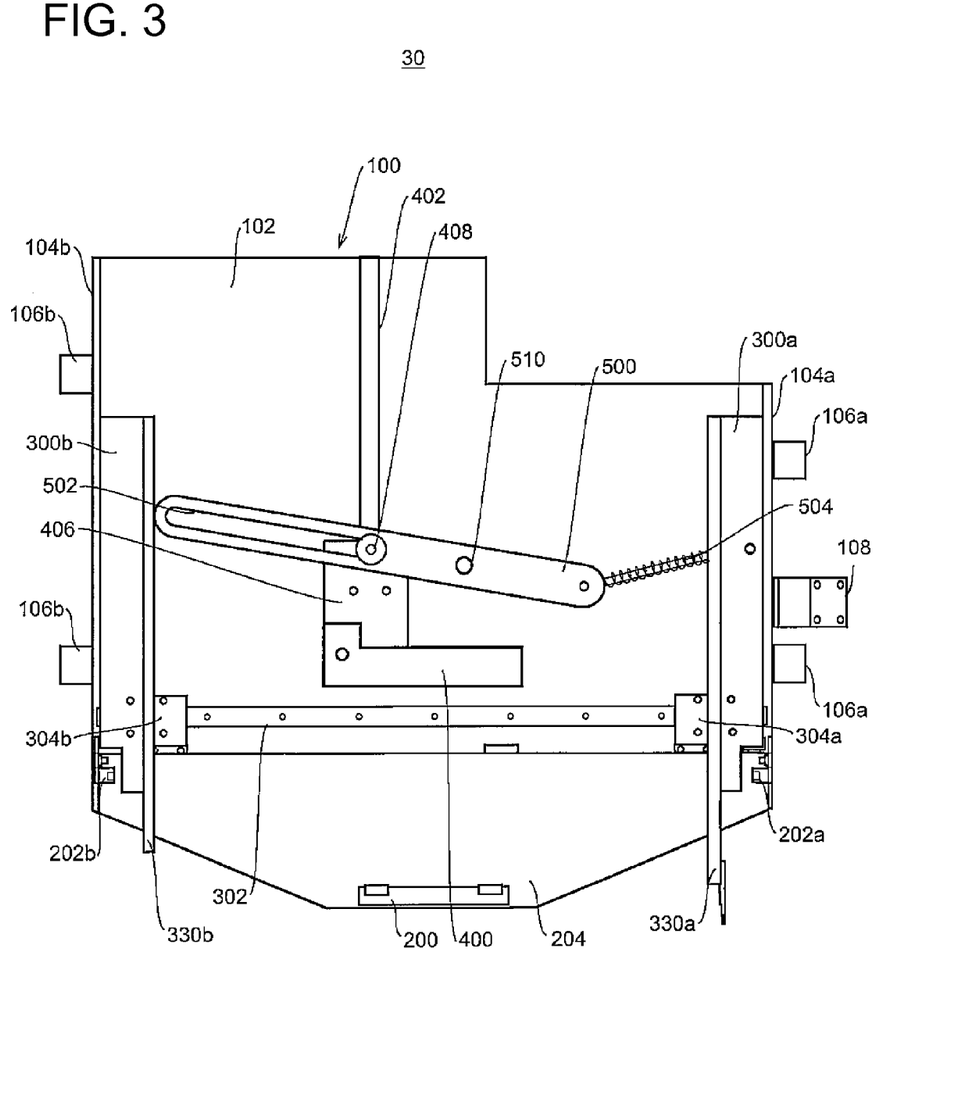
FIG. 3 is a plan view showing a configuration of the cassette tray shown in FIG. 2.
Figure 4:
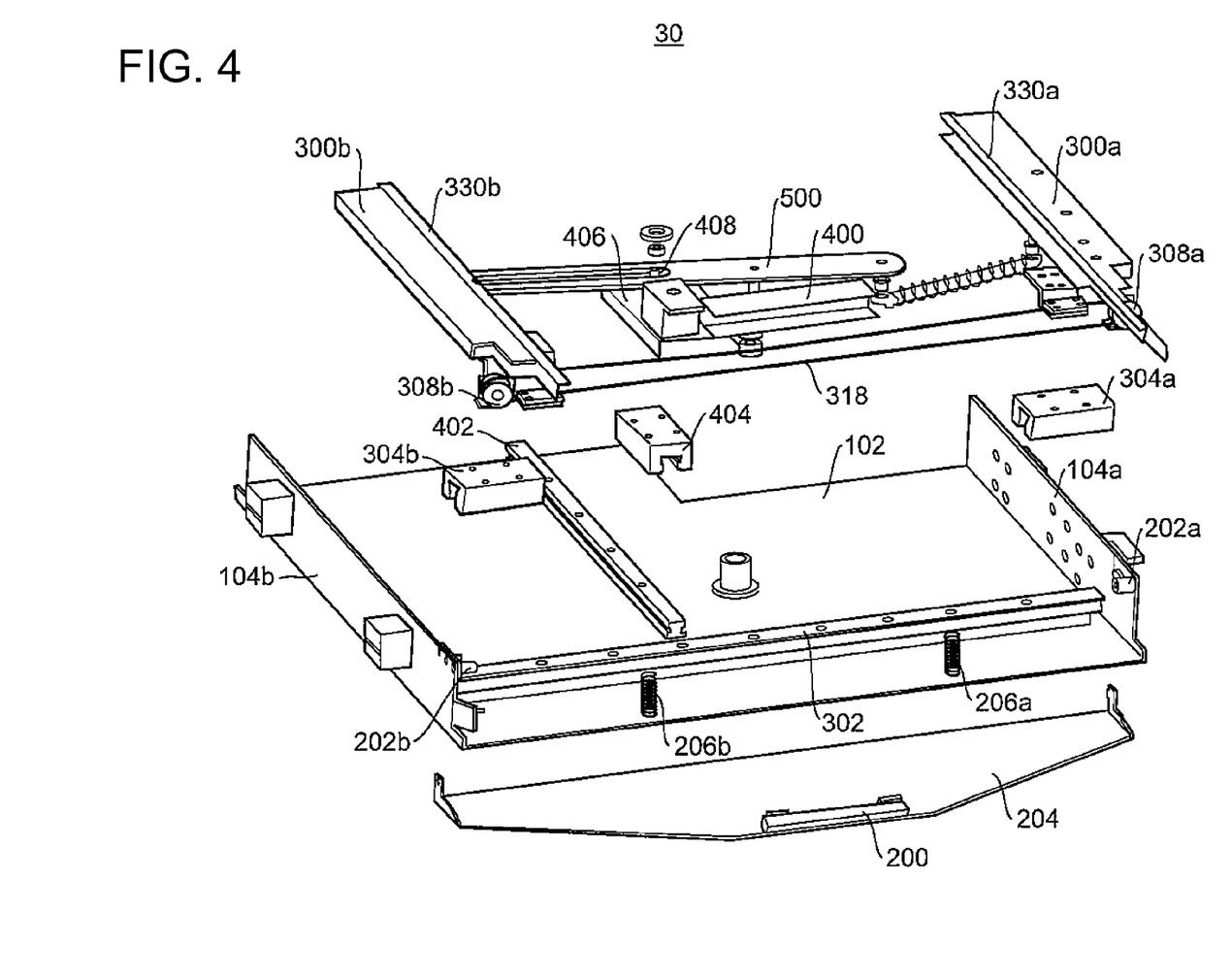
FIG. 4 is an exploded view showing a configuration of the cassette tray shown in FIG. 2.
Figure 5:
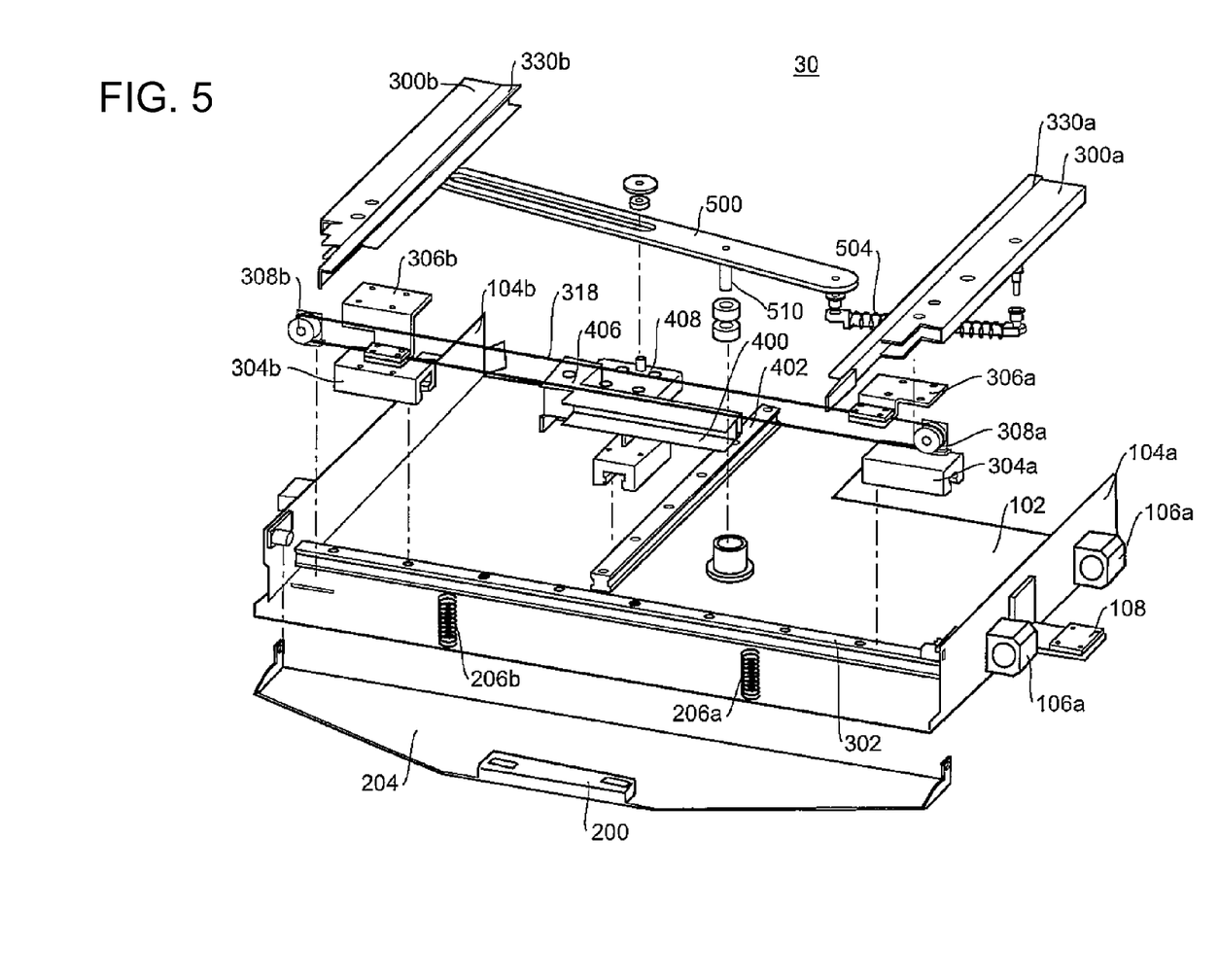
FIG. 5 is an exploded view showing a configuration of the cassette tray shown in FIG. 2.

FIG. 2 is a perspective view, FIG. 3 is a plan view, and FIGS. 4 and 5 are exploded views seen from a different direction. As shown in these figures, the essential part of the cassette tray 30 is composed of a chassis 100 and plural components mounted thereon.

The chassis 100 has a horizontal floor 102 and two vertical walls 104a and 104b standing upright from both sides of the horizontal floor 102. The chassis 100 is engaged with two parallel rails, not shown, by two carriages 106a and 106b provided at the outside of the vertical walls 104a and 104b, and coupled to an unillustrated driving belt with an L metal fitting 108 provided to the vertical wall 104a.

A flip board 204 is mounted to the upper part of the front ends of the vertical walls 104a and 104b through horizontal shafts 202a and 202b. The flip board 204 can be pivoted in the vertical direction about the shafts 202a and 202b.

The flip board 204 is maintained to be horizontal by two springs 206a and 206b arranged between its lower surface and the floor 102. When pushed from above, the flip board 204 pivots downward. It returns to be horizontal with the elimination of the push-down force.

The flip board 204 has a front clamp 200 at its front portion. The front clamp 200 is a member having substantially a rectangular solid that is long in the lateral direction, and is attached to the upper surface of the flip board 204. The front clamp 200 is one example of a front clamp in the present invention. The mechanism composed of the shafts 202a and 202b, the flip board 204, and the springs 206a and 206b is one example of front clamp supporting unit in the present invention.

A lateral rail 302 is provided at the front part of the floor 102 at the far side from the springs 206a and 206b. The direction of the lateral rail 302 is vertical to the vertical walls 104a and 104b. Two carriages 304a and 304b are engaged with the lateral rail 302.

Both-side clamps 300a and 300b are respectively mounted to the carriages 304a and 304b through mounts 306a and 306b. The both-side clamps 300a and 300b are members having substantially a rectangular solid that is long in the longitudinal direction, and extend horizontally in the direction orthogonal to the lateral rail 302. The both-side clamps 300a and 300b are parallel to each other, and are parallel to the vertical walls 104a and 104b. The both-side clamps 300a and 300b are one example of the clamps at both sides in the present invention.

Guides 330a and 330b are mounted to the surfaces of the both-side clamps 300a and 300b that are opposite to each other. The guides 330a and 330b are longitudinal members having an U-shaped cross-section, wherein the opening portions of the U-shape are opposite to each other.

Two pulleys 308a and 308b are mounted at the front part of the floor 102 in front of the both ends of the lateral rail 302. The rotational shafts of the pulleys 308a and 308b are horizontal and parallel to the vertical walls 104a and 104b. A wire 318 is endlessly put around the pulleys 308a and 308b. The wire 318 is an inextensible wire such as, for example, a steel wire. The mounts 306a and 306b are fixedly coupled to the lower part and upper part of the wire 318. The upper part and the lower part of the wire 318 move in the reverse direction with the rotations of the pulleys 308a and 308b. Therefore, the both-side clamps 300a and 300b moves in the direction in which they are apart from each other or in the direction in which they are close to each other.

The mechanism composed of the lateral rail 302, the carriages 304a and 304b, the mounts 306a and 306b, the pulleys 308a and 308b, and the wire 318 is one example of both-side clamp supporting unit in the present invention.

A longitudinal rail 402 is provided at the center of the floor 102. The longitudinal rail 402 is provided at the rear of the lateral rail 302. The longitudinal rail 402 is vertical to the lateral rail 302, and parallel to the vertical walls 104a and 104b.

A carriage 404 is engaged with the longitudinal rail 402. A rear clamp 400 is attached to the carriage 404 through a mount 406. The mount 406 has a vertical pin 408.

The rear clamp 400 is a member having substantially a rectangular solid that is long in the lateral direction, and extends horizontally in the direction orthogonal to the longitudinal rail 402. The rear clamp 400 is opposite to and parallel to the front clamp 200. The plane in which the rear clamp 400 and the front clamp 300 are opposite to each other is the same as the plane in which the both-side clamps 300a and 300b are opposite to each other.

The rear clamp 400 is one example of a rear clamp in the present invention. The mechanism composed of the longitudinal rail 402, the carriage 404 and the mount 406 is one example of rear clamp supporting unit in the present invention.

A lever 500 is mounted at the right side of the longitudinal rail 402. The lever 500 is rotatable in the horizontal plane about a shaft 510. The shaft 510 is provided vertical to the floor 102.

The left arm side of the lever 500 is engaged with the pin 408 on the mount 406 by the slit 502, while the right arm side thereof is coupled to the right clamp 300a by the spring 504. A damper spring is used as the spring 504.

The lever 500 may be provided at the left side of the longitudinal rail 402. In this case, the slit 502 engaged with the pin 408 may be provided at the right arm side, and the left arm side may be coupled to the left clamp 300b through the spring 504.

The rear clamp supporting mechanism and the both-side clamp supporting mechanism are mechanically coupled by the lever 500. With this coupling, the both-side clamps 300a and 300b can move in the direction in which they are apart from each other and in the direction in which they arc close to each other according to the advancing movement and retreating movement of the rear clamp 400. The mechanism composed of the lever 500, the shaft 510, the slit 502, the pin 408 and the spring 504 is one example of driving unit in the present invention.

Figure 6:
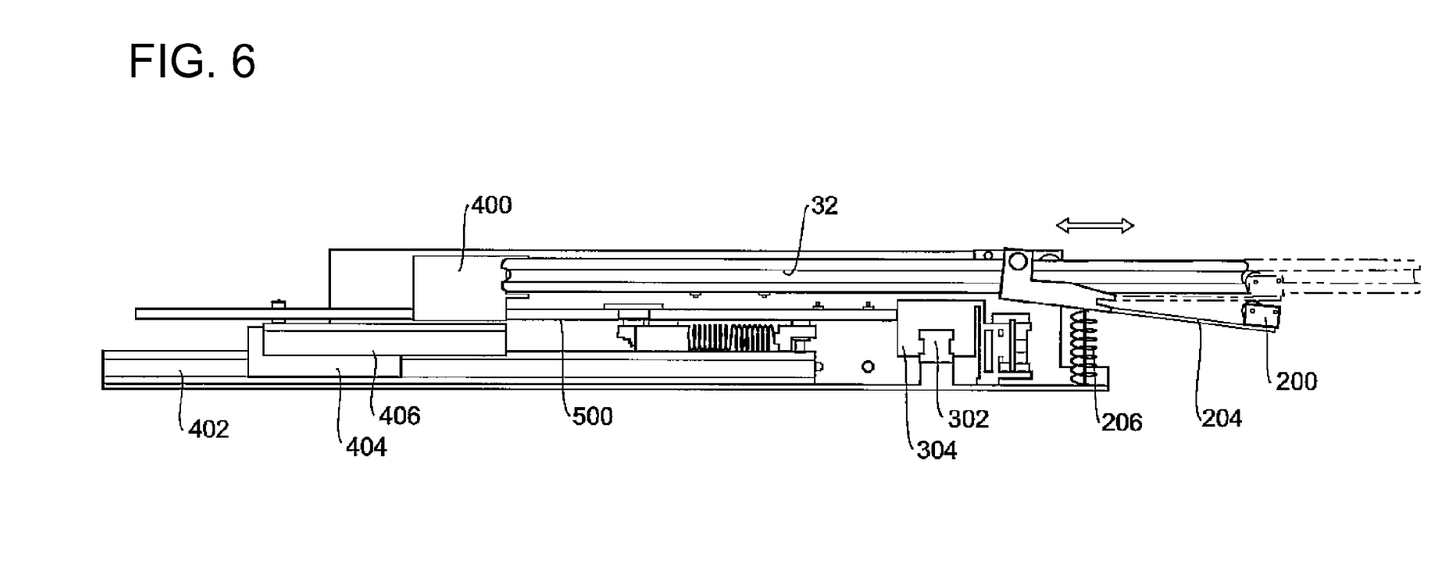
FIG. 6 is a side view showing the state in which the X-ray film cassette is loaded into the cassette tray and the state in which the X-ray film cassette is unloaded from the cassette tray.

FIG. 6 shows the state in which the X-ray film cassette 32 is loaded to or unloaded from the cassette tray 30. In FIG. 6, the leftward arrow indicates the loading direction, while the rightward arrow indicates the unloading direction. An operator loads or unloads the X-ray film cassette 32 into or from the cassette tray 30.

The X-ray film cassette 32 is loaded in such a manner that the front clamp 200 is pushed down by the lower surface of the X-ray film cassette 32 and the rear clamp 400 is pushed to the depth by the trailing end of the X-ray film cassette 32. The rear clamp 400 is pushed in along the guides 330a and 330b provided to the both-side clamps 300a and 300b. The lever 500 rotates in the clockwise direction with the retreating movement of the rear clamp 400 upon pushing in the rear clamp 400, so that the lever 500 pulls the right clamp 300a through the spring 504.

Thus, the both-side clamps 300a and 300b move in the direction in which they are close to each other, whereby they nip the X-ray film cassette 32 from both sides. After nipping the X-ray film cassette 32, the both-side clamps 300a and 300b do not move, and thereafter, the spring 504 stretches with the retreating movement of the rear clamp 400.

When the leading end of the X-ray film cassette 32 passes through the front clamp 200, the flip board 204 returns to be horizontal state by elastic force of the springs 206a and 206b. Thus, the leading end of the X-ray film cassette 32 is clamped by the front clamp 200.

In this way, four sides of the X-ray film cassette 32 are clamped by the front clamp 200, the rear clamp 400 and the both-side clamps 300a and 300b. In the clamped state, compression force caused by the tension of the spring 504 is applied from four sides of the X-ray film cassette 32.

Figure 7A:
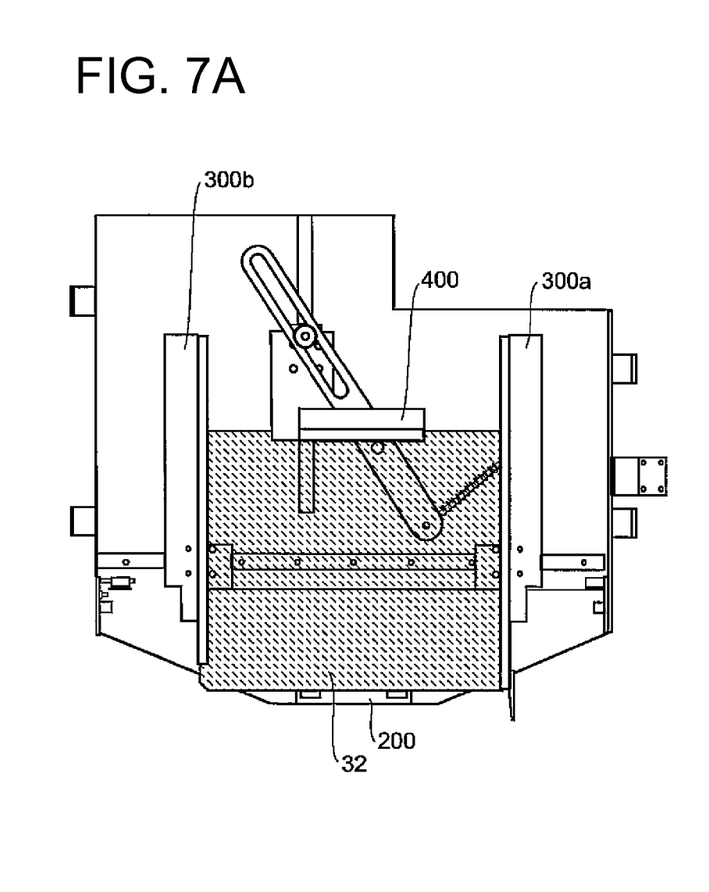
FIGS. 7A and 7B are top views showing the accommodating state of the X-ray film cassette in the cassette tray.
Figure 7B:
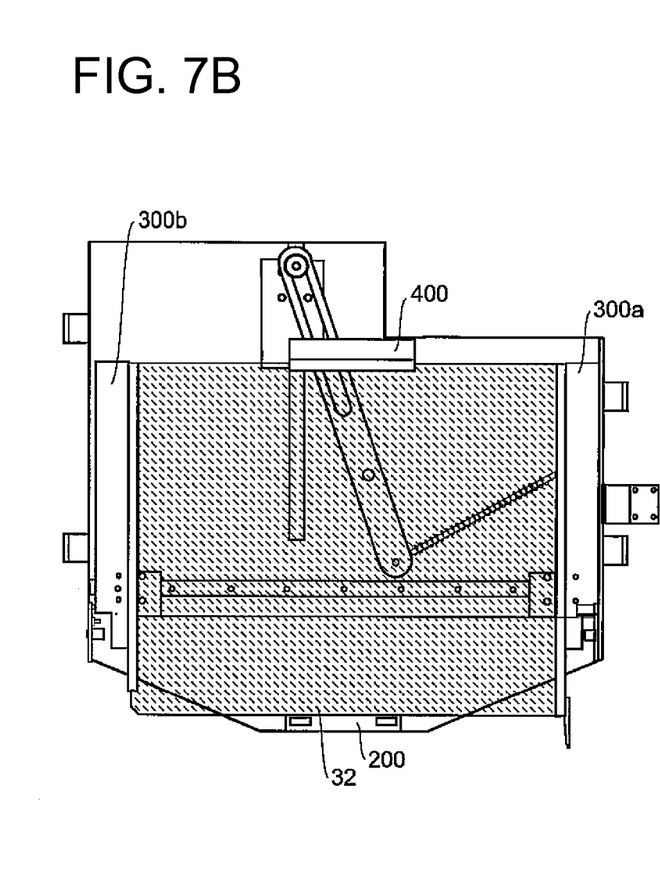

FIGS. 7A and 7B show the accommodating state of the X-ray film cassette 32 in the cassette tray 30. FIG. 7A shows the accommodating state of a small-sized X-ray film cassette, while FIG. 7B shows the accommodating state of a large-sized X-ray film cassette. Since the spring 504 is used, the cassette tray 30 is adaptable to plural X-ray film cassettes having different lateral width.

When the X-ray film cassette 32 is drawn out, the flip board 204 is pushed down to release the clamp of the front side of the X-ray film cassette 32. Then, the rear clamp 400 advances due to the elastic force of the spring 504, thereby pushing out the X-ray film cassette 32.

In this case, the both-side clamps 300a and 300b move in the direction in which they are apart from each other by the counterclockwise rotation of the lever 500 involved with the advancing movement of the rear clamp 400, whereby the clamp of the X-ray film cassette 32 from both sides is released. Since the spring 504 is a damper spring, the X-ray film cassette 32 is slowly drawn out, which unit the X-ray film cassette 32 does not pop out suddenly.

Figure 8A:
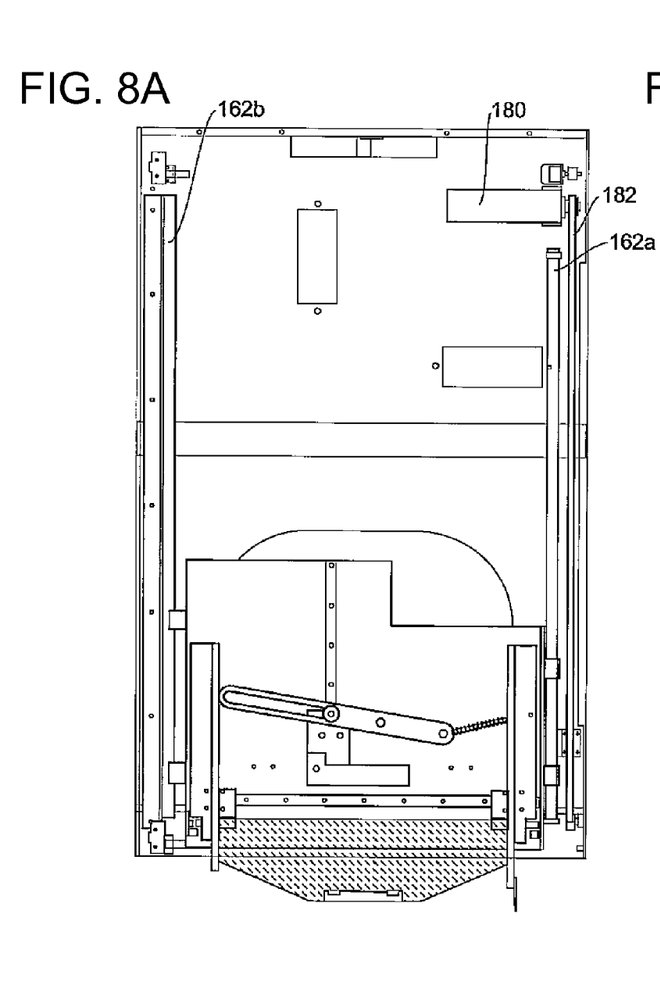
FIGS. 8A and 8B are top views showing the used state and the stand-by state of the cassette tray.
Figure 8B:
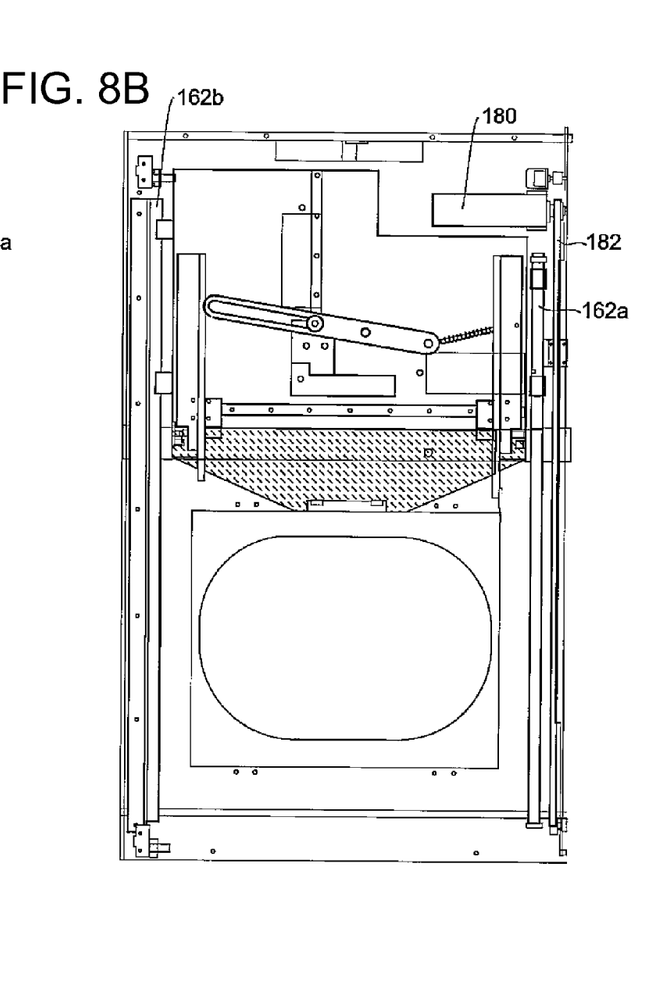

FIGS. 8A and 8B show the used state of the cassette tray 30 and the stand-by state thereof. In the used state, the cassette tray 30 is positioned at the imaging position where the X-ray can be received as shown in FIG. 8A, so that the imaging by unit of the X-ray film cassette is carried out. In the stand-by state, the cassette tray 30 is positioned at the stand-by position where the X-ray film cassette 30 does not block the X-ray as shown in FIG. 8B, so that the imaging using the X-ray detector 40 is carried out.

The carriages 106a and 106b are respectively engaged with the rails 162a and 162b, and the cassette tray 30 is driven by a motor 180 through the belt 182 that is coupled to the L metal fitting 108. The mechanism composed of the rails 162a and 162b, the belt 182, and the motor 180 is one example of moving unit in the present invention.

What is claimed is:

1. A cassette tray configured to regulate and hold an X-ray film cassette by four sides, said cassette tray comprising:
   a front clamp, a rear clamp, and opposing side clamps, each of said front clamp, rear clamp, and said side clamps configured to clamp a front side, a rear side, and two opposing sides of the X-ray film cassette;
   a front clamp supporting unit configured to support said front clamp such that said front clamp is capable of being withdrawn and returned in a direction vertical to a surface of the X-ray film cassette;
   a rear clamp supporting unit configured to support said rear clamp such that said rear clamp is capable of being advanced and retreated in a direction parallel to the surface of the X-ray film cassette;
   a side clamp supporting unit configured to support said side clamps such that said side clamps are movable in a direction in which said side clamps are positioned apart from each other and in a direction in which said side clamps are positioned close to each other; and
   a driving unit configured to drive a spring in the direction in which said side clamps are positioned apart from each other and in the direction in which said side clamps are positioned close to each other according to the advance and retreat of said rear clamp.

2. A cassette tray according to claim 1, wherein said front clamp and said rear clamp are positioned opposite and parallel to each other, said side clamps are positioned opposite and parallel to each other.

3. A cassette tray according to claim 2, wherein said side clamps each comprise a guide to facilitate loading the X-ray film cassette.

4. A cassette tray according to claim 1, wherein said front clamp supporting unit comprises a flip board configured to support said front clamp, and a spring configured to apply a returning force to said flip board.

5. A cassette tray according to claim 1, wherein said rear clamp supporting unit comprises a linear rail to facilitate the advance and retreat of said rear clamp.

6. A cassette tray according to claim 1, wherein said side clamp supporting unit comprises a linear rail to facilitate the movement of said side clamps.

7. A cassette tray according to claim 1, wherein said side clamp supporting unit comprises two pulleys arranged at a space greater than a width of the X-ray film cassette, and a wire that is endlessly put around said pulleys, and to which said side clamps are coupled in such a manner that moving directions caused by rotation of said pulleys are reverse to each other.

8. A cassette tray according to claim 1, wherein said driving unit comprises a lever that configured rotate in a plane parallel to the surface of the X-ray film cassette, wherein said lever comprises a longitudinal slit at a first and that is engaged with a pin and a spring at a second end that is coupled to one of the clamps at both sides said side clamps, said longitudinal slit is configured to move with said rear clamp.

9. A cassette tray according to claim 8, wherein said spring comprises a damper spring.

10. A cassette tray according to claim 1, further comprising a moving unit that configured to integrally move said front clamp supporting unit, said rear clamp supporting unit, said both-side clamp supporting unit, and said driving unit.

11. An X-ray imaging apparatus configured to generate an X-ray fluoroscopic image using an X-ray film cassette loaded to a cassette tray, said X-ray imaging apparatus comprising a cassette tray sized to hold the X-ray film cassette, said cassette tray comprising:
   a front clamp, a rear clamp, and opposing side clamps, each of said front clamp, rear clamp, and said side clamps configured to clamp a front side, a rear side, and two opposing sides of the X-ray film cassette;
   a front clamp supporting unit configured to support said front clamp such that said front clamp is capable of being withdrawn and returned in a direction vertical to a surface of the X-ray film cassette;
   a rear clamp supporting unit configured to support said rear clamp such that said rear clamp is capable of being advanced and retreated in a direction parallel to the surface of the X-ray film cassette;

a side clamp supporting unit configured to support said side clamps such that said side clamps are movable in a direction in which said side clamps are positioned apart from each other and in a direction in which said side clamps are positioned close to each other; and a driving unit configured to drive a spring in the direction in which said side clamps are positioned apart from each other and in the direction in which said side clamps are positioned close to each other according to the advance and retreat of said rear clamp.

12. An X-ray imaging apparatus according to claim 11, wherein said front clamp and said rear clamp are positioned opposite and parallel to each other, said side clamps are positioned opposite and parallel to each other.

13. An X-ray imaging apparatus according to claim 12, wherein said side clamps each comprise a guide to facilitate loading the X-ray film cassette.

14. An X-ray imaging apparatus according to claim 11, wherein said front clamp supporting unit comprises a flip board configured to support said front clamp, and a spring configured to apply a returning force to said flip board.

15. An X-ray imaging apparatus according to claim 11, wherein said rear clamp supporting unit comprises a linear rail to facilitate the advance and retreat of said rear clamp.

16. An X-ray imaging apparatus according to claim 11, wherein said side clamp supporting unit comprises a linear rail to facilitate the movement of said side clamps.

17. An X-ray imaging apparatus according to claim 11, wherein said side clamp supporting unit comprises two pulleys arranged at a space greater than a width of the X-ray film cassette, and a wire that is endlessly put around said pulleys, and to which said side clamps are coupled in such a manner that moving directions caused by rotation of said pulleys are reverse to each other.

18. An X-ray imaging apparatus according to claim 11, wherein said driving unit comprises a lever that configured to rotate in a plane parallel to the surface of the X-ray film cassette, wherein said lever comprises a longitudinal slit at a first end that is engaged with a pin and a spring at a second end that is coupled to one of the clamps at both sides said side clamps, said longitudinal slit is configured to move with said rear clamp.

19. An X-ray imaging apparatus according to claim 18, wherein said spring comprises a damper spring.

20. An X-ray imaging apparatus according to claim 11, further comprising a moving unit that configured to integrally move said front clamp supporting unit, said rear clamp supporting unit, said both-side clamp supporting unit, and said driving unit.

* * * * *